United States Patent [19]

Clouse et al.

[11] Patent Number: 4,496,773

[45] Date of Patent: Jan. 29, 1985

[54] PROCESS FOR THE PREPARATION OF 1,1'-BI-2-NAPHTHOLS

[75] Inventors: Robert C. Clouse; R. Garth Pews, both of Midland, Mich.

[73] Assignee: The Dow Chemical Company, Midland, Mich.

[21] Appl. No.: 479,399

[22] Filed: Mar. 28, 1983

[51] Int. Cl.³ .............................................. C07C 39/14
[52] U.S. Cl. .................................. 568/730; 568/719; 568/722
[58] Field of Search ................ 568/722, 730, 719, 735

[56] References Cited

U.S. PATENT DOCUMENTS

| 3,300,536 | 1/1967 | McNelis | 568/719 |
| 3,876,709 | 4/1975 | Lee et al. | 568/730 |
| 4,067,890 | 1/1978 | Rutledge | 568/730 |
| 4,085,124 | 4/1978 | Rutledge | 568/730 |
| 4,096,190 | 6/1978 | Rutledge | 568/730 |
| 4,097,461 | 6/1978 | Rutledge | 568/730 |
| 4,101,561 | 7/1978 | Rutledge | 568/730 |
| 4,180,686 | 12/1979 | Dodd | 568/730 |
| 4,354,047 | 10/1982 | Strom | 568/730 |
| 4,354,048 | 10/1982 | Strom | 568/730 |

OTHER PUBLICATIONS

Kulawski et al., "Chemical Abstracts", vol. 90; 151874x, (1979).

Primary Examiner—Werren B. Lone
Attorney, Agent, or Firm—Norman L. Sims

[57] ABSTRACT

The invention is a process for coupling 2-naphthols which comprises contacting 2-naphthols dissolved in a polar acidic solvent in the presence of a catalytic amount of a catalyst which comprises a readily reducible form of a Group IB, Group VIII or manganese metal in the further presence of oxygen or a source of oxygen, under conditions such that 1,1'-bi-2-naphthol is prepared.

15 Claims, No Drawings

PROCESS FOR THE PREPARATION OF 1,1'-BI-2-NAPHTHOLS

BACKGROUND OF THE INVENTION

This invention relates to a process for the preparation of 1,1'-bi-2-naphthols.

1,1'-Bi-2-naphthols are useful in the preparation of polyesters and polycarbonates.

Rutledge, U.S. Pat. No. 4,097,461, discloses a process for the coupling of alkylphenols, or 1-naphthols. The coupling products of 1-naphthols are 2,2'-binaphthols and 2,2'-dinaphthenoquinone.

Kulawski et al., Polish Pat. No. 87,440 (Chem. Abs. 90:151874x (1979)), disclose a process for the coupling of naphthols by oxidation in the presence of a stoichiometric amount of an aqueous solution of $FeCl_3$. The products are identified as 4,4'-dihydroxy-1,1'-binaphthol and 1,1'-dihydroxy-2,2'-dinaphthol.

The known processes for the oxidative coupling of naphthols have disadvantages. The formation of dinaphthenoquinones in large amounts as a by-product is a significant disadvantage. The use of stoichiometric amounts of iron ions to promote the oxidation of the naphthols is a further disadvantage. Such large amounts of metal are very costly. Purification of the product is extremely difficult and costly when such large amounts of iron ions are used.

What is needed is a process for the coupling of 2-naphthols to prepare 1,1'-bi-2-naphthols wherein dinaphthenoquinones are not co-produced in significant amounts. What is further needed is a process wherein the metal ions are used in catalytic amounts as opposed to stoichiometric amounts, resulting in a less costly process wherein the purification of the products is simplified.

SUMMARY OF THE INVENTION

The invention is a process for coupling 2-naphthols which comprises contacting 2-naphthols dissolved in a polar acidic solvent in the presence of a catalytic amount of a catalyst which comprises a readily reducible form of a Group IB, Group VIII or manganese metal in the further presence of oxygen or a source of oxygen, under conditions such that 1,1'-bi-2-naphthol is prepared.

This process has significant advantages over the prior art processes. The formation of naphthenoquinone by-products is substantially eliminated. The Group IB, Group VIII metals and manganese are used in catalytic amounts. Thus, the purification of the products is simplified. The process and purification are more economical than the prior art processes.

DETAILED DESCRIPTION OF THE INVENTION

The invention is a process wherein 2-naphthols including those corresponding to the formula

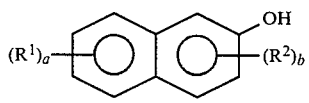

are oxidatively coupled to prepare 1,1'-bi-2-naphthols which include those corresponding to the formula

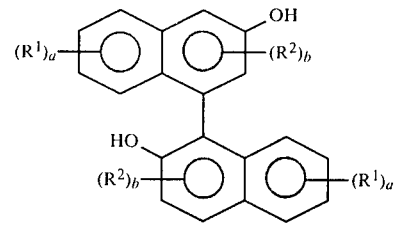

wherein:

$R^1$ is separately in each occurrence a halogen, alkyl, aryl, aryloxy, alkoxy, aralkyl, cyano, nitro or amine group;

$R^2$ is separately in each occurrence a halogen, alkyl, aryl, aryloxy, alkoxy or aralkyl group;

a is separately in each occurrence an integer from 0 to 4, inclusive; and b is separately in each occurrence an integer from 0 to 4, inclusive.

$R^1$ is preferably a halogen, alkyl or aryl group, and most preferably chlorine or bromine. $R^2$ is preferably a halogen, alkyl or aryl group, and most preferably chlorine or bromine. The subscript a is preferably 0 or 1, and most preferably 0. The subscript b is preferably 0 or 1, and most preferably 0.

The solvent is a polar acidic organic compound. It is believed that the use of more acidic solvents results in faster reaction rates. Desirable solvents include acetic acid, trihaloacetic acid, dihaloacetic acid, monohaloacetic acid and methyl sulfonic acid. Preferable solvents include acetic acid, trifluoroacetic acid, difluoroacetic acid, monofluoroacetic acid, trichloroacetic acid, dichloroacetic acid, monochloroacetic acid and methyl sulfonic acid, with acetic acid and trifluoroacetic acid being most preferred.

The catalyst is a readily reducible form of a Group IB, Group VIII or manganese metal. Readily reducible form means herein that the metal will undergo an oxidation-reduction reaction with the 2-naphthol in which the 2-naphthol is oxidized. In such cases, the metals are present as positive ions wherein the metals are in their most stable oxidation state, usually either +3 or +2. Masterton et al., *Chemical Principles*, 3rd Ed., p. 539, W. B. Saunders Co. (1973), illustrate the available and most stable oxidation states of the Group IB, Group VIII and manganese metals (incorporated herein by reference). The preferred catalysts are cobalt, manganese and iron in the reducible form, with iron most preferred. The valence states of iron and cobalt can be +3 or +2 with +3 preferred. The valence states of manganese can be +7, +4, +3 or +2 with +2 most preferred.

The source of the catalysts can be any compound which contains the metal catalyst in a readily reducible form as defined above provided the compound is soluble in the reaction solvent, for example, metal oxides, metal hydroxides, metal salts, metal cyanides, or metal cyanide complexes. Examples of metal salts include, metal halides, metal carbonates, metal acetates, metal sulfides and metal sulfates. Usually salts of the metal catalysts are good sources, for example, metal halides such as $FeCl_3$ and metal acetates, such as cobalt acetate. Trace amounts of catalyst will catalyze the reaction but the rate would be unreasonably low. Stoichiometric amounts of catalyst can be used, but in such a case, the Group IB, Group VIII and manganese metals above would not be catalytic and the disadvantages described above would be experienced. Desirable amounts of catalyst are between about 0.1 and 10 mole percent based on the 2-naphthols. Preferably, amounts are between 1 and 5 mole percent, with 2 to 3 mole percent most preferred.

In the process described herein, the 2-naphthols are dissolved in the solvent along with a catalytic amount of a catalyst. The reaction mixture is contacted with oxygen or a source of oxygen. A source of oxygen means herein any mixture which contains oxygen, for example air. The presence of oxygen is necessary to render the Group IB, Group VIII or manganese metal catalytic. It is believed that the oxygen oxidizes the metal catalyst, after the metal catalyst is reduced in the oxidation of the 2-naphthol. It is further believed that the metal catalyst upon oxidation is then available to oxidize the 2-naphthol. It is also believed that the continued oxidation of the Group IB, Group VIII or manganese metal after it is reduced in the process renders the metal catalytic. The reaction mixture may be contacted with oxygen by several methods. In one embodiment, the reaction can be carried out in a reaction vessel pressurized with oxygen. In this embodiment, the use of higher pressures results in faster reaction rates because more oxygen is available. In another embodiment, oxygen can be bubbled through the reaction mixture.

It is preferable to run the reaction under anhydrous conditions, as the presence of water aids the formation of the binaphthenoquinone by-products.

Desirable temperatures are those temperatures at which the reaction proceeds. Preferable temperatures are between about 0° C. and 200° C. More preferable temperatures are between about 35° C. and 75° C. Below 35° C. the reaction rate is very slow. Above 75° C. formation of polymerization products is often observed. At lower temperatures, the selectivity of the reaction for the 1,1'-bi-2-naphthols is enhanced, whereas the rate of conversion of the starting reactants is lower than at higher temperatures.

Pressures for this process can be atmospheric or superatmospheric. At superatmospheric pressures, oxygen or a source of oxygen is usually used to pressurize the reactor.

Desirable reaction times include between 10 and 24 hours, although longer or shorter reaction times can be used. The reaction time is affected by the catalyst amount or reaction temperature. If either is increased, the reaction time for a particular conversion is reduced.

The product can be purified by washing it with hot water to remove the unreacted 2-naphthols, as the 2-naphthols are soluble in water but the 1,1'-bi-2-naphthols are not. The residual catalyst can be removed by washing the product with an aqueous solution containing about 5 to 15 percent by weight of a phosphate.

SPECIFIC EMBODIMENTS

The following examples are included for the purpose of illustrating the invention described herein, and do not limit the scope of the invention or the claims. In the following examples, all parts and percentages are based on moles unless otherwise specified.

EXAMPLE 1

To a Hastelloy ®C bomb (total volume 200 ml) is charged 10.0 g of 2-naphthol, 0.25 g of FeCl$_3$ and 50 ml of trifluoroacetic acid. The bomb is pressurized to 190 psig with oxygen, and the temperature is elevated to 38° C. After 35 hours, a sample taken from the reaction mixture is analyzed by liquid chromatography. The conversion of 2-naphthols to products is 35.8 mole percent. 92.3 Mole percent of the products is 1,1'-bi-2-naphthol.

EXAMPLE 2

To a Hastelloy ®C bomb reactor (200 ml total volume) is added 10.0 g of 2-naphthol, 0.7 g of CuCl and 50 ml of trifluoroacetic acid. The bomb is pressurized to 190 psig with oxygen. With stirring, the temperature is elevated to 72° C. and held for 4 hours. Thereafter, a sample from the bomb is analyzed by liquid chromatography. With an 88.6 percent mass balance, the analysis shows that 45 percent of the 2-naphthol is converted to products. The product contains 74.7 percent of 1,1'-bi-2-naphthol.

EXAMPLE 3

The experiment described in Example 2 is repeated except the temperature is 62° C. and the reaction time is 6 hours. The liquid chromatographic analysis shows a conversion of 2-naphthol to products of 41.9 percent, of which 52.0 percent is 1,1'-bi-2-naphthol with a mass balance of 79.7 percent.

EXAMPLE 4

To a Hastelloy ®C bomb reactor (200 ml total volume) is added 10.0 g of 2-naphthol, 5 mole percent of cobalt acetate based on the 2-naphthol and 50 ml of trifluoroacetic acid. The bomb is pressurized with 190 psig of oxygen. With stirring the temperature of the reactor is raised to 60° C. and held at that temperature for 6 hours. Analysis of the product by liquid chromatography shows a 70.0 percent conversion of the 2-naphthol. The product contains 58.3 percent of 1,1'-bi-2-naphthol with a mass balance of 65.2 percent.

EXAMPLE 5

To a Hastelloy ®C bomb reactor (200 ml total volume) is charged 10.0 g of 2-naphthol, 50 ml of trifluoroacetic acid and 5 mole percent of manganese acetate. The bomb is pressurized to 185 psig with oxygen. The reactants are reacted at 60° C. for 6 hours with stirring. Analysis of the product by liquid chromatograph shows a 52.0 percent conversion of 2-naphthol to products. The product contains 38.5 percent of 1,1'-bi-2-naphthol with a 58.3 percent mass balance.

EXAMPLE 6

To a Hastelloy ®C bomb reactor (200 ml total volume) is charged 20.0 g of 2-naphthol, 0.4 g of FeCl$_3$ and 50 ml of acetic acid. The bomb is pressurized to 200 psig with oxygen. The contents are reacted at 50° C. for 10 hours. Analysis of the product by liquid chromatograph shows a 45.0 percent conversion of 2-naphthol. The product contains 74.0 percent of 1,1'-bi-2-naphthol with an 88.1 percent mass balance. No binaphthenoquinones were detected in the product by liquid chromatography, precision about 1 percent.

EXAMPLE 7

To a Hastelloy ®C bomb reactor (200 ml total volume) is charged 6.0 g of 2-naphthol, 0.5 g of FeCl$_3$ and 50 ml of trifluoroacetic acid. The reactor is pressurized to 200 psig with oxygen. The contents are reacted at 58° C. for 10 hours. The product is washed, extracted with $CH_2Cl_2$ and dried over $CaSO_4$. The $CH_2Cl_2$ is stripped off. The product is then dissolved in $CH_3CN$. Liquid chromatographic analysis of the product shows a 93.8 percent conversion of the 2-naphthol to products. The product contains 82.7 percent of 1,1'-bi-2-naphthol with an 83.9 percent mass balance. No binaphthenoquinones were detected in the product by liquid chromatography, precision 1 percent.

What is claimed is:

1. A process for coupling 2-naphthols which comprises contacting a 2-naphthol dissolved in a polar acidic organic solvent in the presence of a catalytic amount of a catalyst which comprises a readily reducible form of a Group IB, Group VIII or manganese metal in the further presence of oxygen or a source of oxygen at a temperature between 0° and 200° C. under conditions such that a 1,1'-bi-2-naphthol is prepared wherein the product contains less than about 1 mole percent of binaphthenoquinones.

2. The process of claim 1 wherein the reaction is run under substantially anhydrous conditions.

3. The process of claim 1 wherein the 2-naphthols correspond to the formula

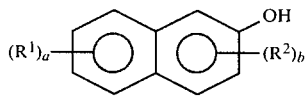

and the 1,1'-bi-2-naphthols correspond to the formula

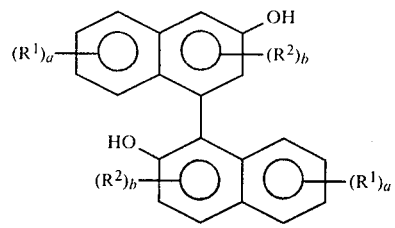

wherein:
$R^1$ is separately in each occurrence a halogen, alkyl, aryl, aryloxy, alkoxy, aralkyl, cyano, nitro or amine group;
$R^2$ is separately in each occurrence a halogen, alkyl, aryl, aryloxy, alkoxy or aralkyl group;
a is separately in each occurrence an integer from 0 to 4, inclusive; and
b is separately in each occurrence an integer from 0 to 4, inclusive.

4. The process of claim 3 wherein $R^1$ is a halogen, alkyl or aryl group and $R^2$ is a halogen, alkyl or aryl group.

5. The process of claim 4 wherein $R^1$ and $R^2$ are chlorine or bromine.

6. The process of claim 3 wherein a is 0 or 1 and b is 0 or 1.

7. The process of claim 6 wherein a and b are 0.

8. The process of claim 1 wherein the catalyst is cobalt, manganese or iron.

9. The process of claim 8 wherein the catalyst is iron.

10. The process of claim 1 wherein the mole percentage of catalyst is between about 0.1 and 10 percent.

11. The process of claim 10 wherein the mole percentage of catalyst is between about 1 and 5 percent.

12. The process of claim 1 wherein the solvent is acetic acid, trihaloacetic acid, dihaloacetic acid, monohaloacetic acid or methyl sulfonic acid.

13. The process of claim 12 wherein the solvent is acetic acid, trifluoroacetic acid, difluoroacetic acid, monofluoroacetic acid, trichloroacetic acid, dichloroacetic acid, monochloroacetic acid or methyl sulfonic acid.

14. The process of claim 13 wherein the solvent is acetic acid or trifluoroacetic acid.

15. The process of claim 1 wherein the temperature is between about 35° C. and 75° C.

* * * * *